United States Patent [19]

Powell

[11] Patent Number: 4,606,753
[45] Date of Patent: Aug. 19, 1986

[54] 4-SUBSTITUTED-2-OXABICYCLO[2.2.1]HEPTANE ETHER HERBICIDES

[75] Inventor: James E. Powell, Ripon, Calif.

[73] Assignee: Shell Oil Company, Houston, Tex.

[21] Appl. No.: 621,011

[22] Filed: Jun. 15, 1984

[51] Int. Cl.$^4$ .................. A01N 43/00; C07D 311/00
[52] U.S. Cl. .......................................... 71/88; 71/92; 71/94; 544/335; 546/269; 549/397; 549/414; 549/415; 549/463
[58] Field of Search ............... 549/397, 463; 71/88

[56] References Cited

U.S. PATENT DOCUMENTS

| | | | |
|---|---|---|---|
| 3,753,678 | 8/1973 | Young et al. | 71/88 |
| 4,410,354 | 10/1983 | Sundelin et al. | 71/94 |
| 4,439,225 | 3/1984 | Kollmeyer | 71/88 |
| 4,486,219 | 12/1984 | Powell | 71/88 |
| 4,486,220 | 12/1984 | Payne | 71/88 |
| 4,487,945 | 12/1984 | Payne | 549/463 |
| 4,525,203 | 6/1985 | Payne et al. | 549/397 |
| 4,542,244 | 9/1985 | Payne et al. | 568/825 |

FOREIGN PATENT DOCUMENTS

| | | |
|---|---|---|
| 81892 | 6/1983 | European Pat. Off. ............ 549/463 |
| 81893 | 6/1983 | European Pat. Off. . |
| 2937645 | 4/1981 | Fed. Rep. of Germany . |

OTHER PUBLICATIONS

Payne et al., Chem. Abst. 99: 212423j.

Primary Examiner—Donald G. Daus
Assistant Examiner—Cecilia Shen

[57] ABSTRACT

Novel oxabicycloalkane ether of the formula

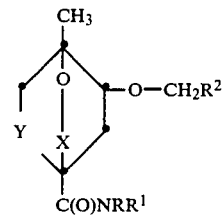

wherein X is a single bond or —C(CH$_3$)$_2$— and Y is a single bond or —CH$_2$— with the proviso that both X and Y are not a single bond; R is H or —C(O)R$^3$ in which R$^3$ is H or certain hydrocarbyl groups; R$^1$ is certain hydrocarbyl groups, or certain derivatives thereof, such as esters or carbamoyl compounds; and R$^2$ is cyano or certain unsaturated, aromatic, heterocyclic, cycloalkyl, cycloalkenyl or secondary alkyl group, are useful as herbicides or plant growth regulators.

12 Claims, No Drawings

4-SUBSTITUTED-2-OXABICYCLO[2.2.1]HEPTANE ETHER HERBICIDES

BACKGROUND OF THE INVENTION

Field of the Invention

The present invention relates to novel oxabicycloalkane ether herbicides, their use as herbicides and plant growth regulators, and to compositions containing these novel ethers.

SUMMARY OF THE INVENTION

The present invention is directed to compounds of the formula 1

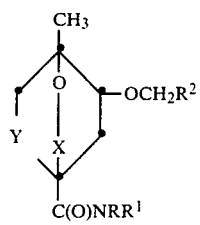

wherein R is H or —C(O)R$^3$ in which R$^3$ is a hydrogen atom, an alkyl group containing 1 to 6 carbon atoms, an alkenyl or alkynyl group containing 3 to 4 carbon atoms, each optionally substituted by one or more halogen atoms, or an aryl group, aralkyl group or heterocyclic group in which the one or two hetero atoms are N or O, each group containing up to 14 carbon atoms and optionally ring-substituted by one or more halogen atoms or alkyl groups containing from 1 to 4 carbon atoms; R$^1$ is

in which R$^3$ has the above meaning and R$^4$ is a hydrogen atom or an alkyl group containing from 1 to 6 carbon atoms, —SO$_2$R$^3$ in which R$^3$ has the above meaning, —P(O)(ZR$^3$)$_2$ in which Z is O, N or S, and R$^3$ has the above meaning, —C(O)R$^3$ in which R$^3$ has the above meaning; —OR$^3$ in which R$^3$ has the above meaning;

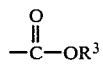

in which R$^3$ has the above meaning; or (1,3,3-trimethyl-6-(phenylmethoxy)-2-oxabicyclo[2.2.1]heptan-4-yl)-carbonylaminocarbonyl; or R and R$^1$ when taken together are =C=O; X is a single bond or —C(CH$_3$)$_2$— and Y is a single bond or —CH$_2$— with the proviso that both X and Y are not a single bond; and R$^2$ is an optionally substituted unsaturated hydrocarbon group containing 2 to 4 carbon atoms, an aromatic group containing up to 14 carbon atoms, or a heterocyclic group in which the one or two heteroatoms are each selected from O, S or N containing up to 14 carbon atoms; a cyano group, a cycloalkenyl group containing 5 to 7 carbon atoms; a cycloalkyl group containing 3 to 10 carbon atoms optionally substituted by alkyl of 1 to 3 carbon atoms; or a secondary alkyl group containing 3 to 10 carbon atoms, and stereoisomer forms or mixtures thereof. The compounds of formula 1 are useful as herbicides or plant growth regulators except when R and R$^1$ are taken together as =C=O to give compounds which are intermediates to the active compounds of formula 1.

Optional substituents for each R$^2$ group inclue hydroxy; cyano; halogen atoms having an atomic number of from 9 to 35, inclusive; or alkyl, optionally substituted by hydroxy, amino, alkanoylamino, alkoxy or alkylthio; haloalkyl, alkoxy, haloalkoxy, alkylthio, haloalkylthio, alkylsulfinyl, alkylsulfonyl, alkenyl or alkynyl of up to 4 carbon atoms; an aminocarbonyl, carboxyl, amino, or alkanoylamino, each of which hydrogen can be substituted for by alkyl of 1 to 4 carbon atoms; or equivalent kinds of substituents. Preferably, the optional substituent is an alkyl group containing 1 or 2 carbon atoms, especially a methyl group.

Compounds that possess substantially the same plant growth regulator or herbicidal utility as those described above and can be prepared in like manner are equivalents thereof and include compounds wherein, for example, R$^2$ is an optionally-substituted, unsaturated hydrocarbyl, cyclohexyl, cycloalkyl, secondary alkyl, mono- or polycyclic aromatic or saturated or unsaturated heterocyclic moiety or the like or equivalents thereof, including but not limited to cyano, cyclopropyl or 1-methylcyclopropyl, naphthyl, imidazolyl, triazolyl, thiadiazolyl, 2-quinolinyl, 1-isoquinolinyl, pyrrolyl, cyclohexenyl, N-methylimidazolyl, N-methylpyrazolyl, isoxazolyl, oxazolyl, isothiazolyl, thiazolyl, thienyl, 5-methyl-2-furanyl, tetrahydro-2-pyranyl and the like.

Non-limiting embodiments of the compounds of formula 1 of the invention include 6-(Pyridin-2-ylmethoxy)-4-((phenoxycarbonyl)aminocarbonyl)-1,3,3-trimethyl-2-oxabicyclo[2.2.-2]octane, 6-Propargyloxy-4-((propylsulfonyl)aminocarbonyl)-1,3,3-trimethyl-2-oxabicyclo[2.2.1]heptane, 6-(Sec-butylmethoxy)-4-(benzyloxyaminocarbonyl)-1,3,3-trimethyl-2-oxabicyclo[2.2.1]heptane, 6-(Cyclohexenylmethoxy)-4-((ethylaminocarbonyl)aminocarbonyl)-1,3,3-trimethyl-2-oxabicyclo[2.2.1]heptane, 2-(2-Methybenzyloxy)-1-methyl-4-((diethoxyphosphinyl)aminocarbonyl)-7-oxabicyclo[2.2.1]heptane, 2-(Pyrimidin-4-ylmethoxy)-4-((methoxycarbonyl)aminocarbonyl)-1-methyl-7-oxabicyclo[2.2.1]heptane, 2-(Cyanomethoxy)-4-((propargylaminocarbonyl)aminocarbonyl)-1-methyl-7-oxabicyclo[2.2.1]heptane, and the like.

In one embodiment of the invention, R is a hydrogen atom; and R$^1$ is

in which R$^3$ is an alkyl group containing 1 to 4 carbon atoms or an alkenyl or alkynyl group containing 3 to 4 carbon atoms and R$^4$ is a hydrogen atom; —OR$^3$ in which R$^3$ is an alkyl group containing 1 to 4 carbon atoms; or —C(O)R$^3$ in which R$^3$ is an alkyl group containing 1 to 4 carbon atoms; and when R$^1$ is —C(O)R$^3$ then R is also additionally —C(O)R$^3$. Preferably, R is a hydrogen atom; and R$^1$ is

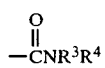

in which $R^3$ is an alkyl group of 1 to 4 carbon atoms; allyl or propargyl and $R^4$ is a hydrogen atom; —$OR^3$ in which $R^3$ is a methyl or ethyl group; or —$C(O)R^3$ in which $R^3$ is a methyl or ethyl group and when $R^1$ is —$C(O)R^3$ then R is also additionally —$C(O)R^3$.

In another embodiment of the invention, R is a hydrogen atom and $R^1$ is —$P(O)(OR^3)_2$ in which $R^3$ is an alkyl group containing 1 to 4 carbon atoms. Preferably, $R^3$ is an ethyl group.

In one embodiment of the invention, $R^2$ is an ethynyl group; a phenyl group optionally substituted by one or two halogen atoms of atomic number of 9 or 17 or by a methyl group; or a 5- or 6-membered saturated or unsaturated heterocyclic group containing one or two heteroatoms of O or N optionally-substituted by alkyl containing 1 or 2 carbon atoms. Preferably, $R^2$ is phenyl, 2-chlorophenyl, 2-fluorophenyl, 2-methylphenyl, 2,6-dichlorophenyl, 4-fluorophenyl, pyridin-2-yl, pyrimidin-4-yl, tetrahydropyran-2-yl, furan-2-yl, tetrahydrofuran-2-yl or the like. The compounds wherein $R^2$ is phenyl, 2-fluorophenyl, 2-methylphenyl or tetrahydropyran-2-yl are a preferred embodiment of the compounds of formula 1.

The Compounds of the Invention described by formula 1 are prepared by treating the appropriately substituted oxabicycloalkanol with a compound of the formula $R^2CH_2X$ in which X is a halogen atom, such as bromine, chlorine or iodine, or is a hydrocarbylsulfonyloxy group, e.g. a mesyloxy, tosyloxy group or the like, preferably in the presence of a strong base and an inert diluent. The strong base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

The compounds $RCH_2X$, in which R and X are defined above, are generally known in the art, for example, as in U.S. Pat. No. 3,753,678 and co-pending U.S. Ser. No. 416,572, filed Sept. 13, 1982, as a continuation-in-part of abandoned Ser. No. 331,094, filed Dec. 16, 1981, and the like, and are prepared by conventional procedures known in the art. For example, the tetrahydro-2-pyranylmethanol derivatives R—$CH_2X$ in which X is a halogen atom, or hydrocarbylsulfonyloxy group and R is a tetrahydro-2-pyranyl group optionally ring-substituted by one or more alkyl groups are generally known in the art and are readily prepared from the tetrahydro-2-pyranylmethanols, by conventional methods known in the art for preparing halides and sulfonates of alcohols. For example, the tetrahydro-2-pyranylmethanol tosylate is described in R. J. Palmer et al., *J. Amer. Chem. Soc.*, 102 (27) pages 7888–92 (1980) as well as its preparation. The alkyl tetrahydro-2-pyranylmethanols are known materials or can be prepared by literature methods, including application of the methods of G. Buchi and J. E. Powell, *J. Am. Chem. Soc.*, 92, 3126 (1970), E. L. Eliel, M. Manoharan, K. M. Pietrusiewicz, K. D. Hargrave, *Org. Magn. Res.*, 21, 94 (1983); E. L. Eliel, K. D. Hargrave, K. M. Pietrusiewicz, M. Manoharan, *J. Am. Chem. Soc.*, 104, 3635 (1982), J. Jurczak and M. Tkacz, *J. Org. Chem.*, 44, 3347 (1979) and the like.

The substituted oxabicycloalkanol reactants are obtained generally by one or more of the following routes: directly by (a) epoxidation-cyclization of unsaturated cyclic alcohols, with or without isolation of epoxy alcohol intermediates; and indirectly by (b) Diels-Alder reactions of furans with dienophiles.

Detailed routes are described below.

In (a), the epoxidation-cyclization of unsaturated cyclic alcohols involves treatment in an inert solvent by an oxidizing agent in the presence or subsequent addition of an acid. The alcohols are either (i) cycloalk-3-en-1-ols, or (ii) cycloalk-3-ene-1-methanols. The cycloalk-3-en-1-ols are prepared from spiro(3-cyclohexene-1,2-oxiranes): by reduction; by addition of HCN; by rearrangement; by reduction; by treatment with a Grignard reagent; or by hydrogenating and then dealkylating or hydrolyzing, respectively, Diels-Alder adducts of vinyl ethers or esters prepared from dienes, such as isoprene, and vinyl ether or ester dienophiles in which the alpha-position of the vinyl group is substituted by alkyl, CN, $CO_2R^5$, or $CON(R^5)_2$ in which $R^5$ is a lower alkyl group. The cycloalk-3-ene-1-methanols are (1) Diels-Alder adducts of allylic alcohols; or (2) products obtained from Diels-Alder adducts of alpha-beta unsaturated carbonyl compounds, such as acrylates, crotonates, aldehydes or ketones, by reduction or treatment with a Grignard reagent.

In (b), the Diels-Alder type adducts of furans with dienophiles may require vigorous reaction conditions, including high pressure and low temperature, for example, as described in Dauben, W. G. et al., *J. Amer. Chem. Soc.*, 102, page 6894 (1980). When the dienophile is nitroethylene, the resulting product is hydrogenated, then oxidized to the ketone and reduced to the corresponding alcohol, e.g. by treatment with a hydride or metal. When this alcohol has the endo form, it can be epimerized with base or aluminum isopropoxide in the presence of a ketone to the corresponding exo alcohol.

Endo- and exo-oxabicycloalkanol intermediates can be separated by conventional methods, such as crystallization, chromatography and the like, and the geometric forms can be resolved by classical resolution methods to give a substantially pure single isomer.

Non-limiting illustrations of the preparations of representative Compounds of the Invention follow.

The compounds of formula 1 are prepared from the corresponding oxabicycloalkanols of the formula 1a

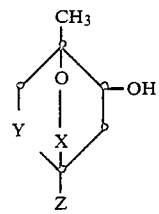

in which Z is acetyl, —CN or $CO_2R$ in which R is H or lower alkyl, C(O)Hal, or —$C(O)NR_2$ in which R is H or lower alkyl. Depending on the ring system, it may be easier to make the —CN derivative and convert it by conventional methods to the —C(O)NH$_2$ derivative or vice versa. In any of the ring systems, the derivatives in which Z is —CN or —C(O)NH$_2$ are versatile for synthesizing the ether compounds of formula 1. Following etherification with the desired R$^2$ groups, the Z=—C(O)NH$_2$ group is derivatized as follows.

(a) and R$^1$ together are =C=O by treating the aminocarbonyl substituted ether with oxalyl chloride, preferably in a solvent at ambient temperatures or slightly higher; (b) R=H and R$^1$=C(O)NHR$^3$ by treating the acyl isocyanate of (a) with the amine corresponding to HNHR$^3$ in a solvent, such as methylene chloride at ambient temperatures; (c) R=H and R$^1$=OR$^3$ or SO$_2$R$^3$ by first converting the amide in two steps to the corresponding acid halide —C(O)Hal using conventional methods and then treating these derivatives with the amine compound corresponding to H$_2$NOR$^3$, e.g. methoxyamine, or an amide such as methanesulfonamide and the like; (d) R=H and R$^1$=P(O)(ZR$^3$)$_2$, —C(O)OR$^3$, —C(O)R$^3$ by treating the unsubstituted amide with a halide of the group to be introduced, e.g. acetyl halide, diethyl chlorophosphate, ethyl chloroformate and the like.

In one embodiment, the compounds of formula 1, wherein X is a single bond and Y is —CH$_2$—, having the formula I

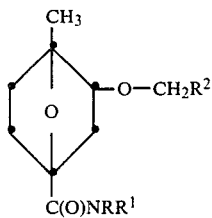

can be prepared from 7-oxabicyclo[2.2.1]heptan-2-ols and ethers of formula 1a, wherein the 4-position is substituted by Z, as defined above for formula 1a, which alcohols and ethers are obtained from cyclohex-3-en-1-ols or by epoxidation-cyclization.

The epoxidation of cyclohex-3-en-1-ols into the corresponding epoxy-alcohol is effected by action of an oxidizing agent, particularly a peroxide, such as m-chloroperbenzoic acid, peracetic acid, tert-butyl hydroperoxide (TBHP) or equivalent peroxide reagents. Preferably, the oxidation with TBHP is conducted in the presence of an appropriate transition metal catalyst, e.g. vanadium. Preferably, the complex is an organic complex, for example, with beta-diketones, o-hydroxybenzaldehydes or o-hydroxybenzphenones and particularly with acetylacetone, for example, vanadium(IV) bis(2,4-pentanedionate) oxide is preferred. The reaction is suitably conducted in the presence of an inert solvent such as chlorinated hydrocarbons, ethers, hydrocarbons or the like. Suitable chlorinated hydrocarbons contain from 1 to 4 chlorine atoms in combination with an alkane chain containing from 1 to 4 carbon atoms or a benzene ring, for example, carbon tetrachloride, chloroform, dichloromethane, chlorobenzene and 1,2- or 1,3-dichlorobenzene and the like. Ethers are generally those containing from 4 to 6 carbon atoms, for example, diethyl ether, methyl tert-butyl ether and diisopropyl ether. Tetrahydrofuran and dioxane are also useful. Suitable alkanes contain from 5 to 10 carbon atoms, for example, n-pentane, n-hexane, n-heptane, n-octane, n-nonane, n-decane and their isomers. Petroleum fractions rich in alkanes are also suitable. Petroleum ether is also suitable. Cyclohexane and methylcyclohexane are examples of useful cycloalkane solvents containing from 6 to 8 carbon atoms. Suitable aromatic hydrocarbon solvents contain from 6 to 10 carbon atoms, for example, benzene, toluene, o-, m-, and p-xylene, the trimethylbenzenes, p-ethyltoluene and the like. The reaction is conducted at temperatures conveniently in the range of from about −10° C. to about 50° C. or slightly above. Generally, the temperature is from about −5° C. to about 40° C., preferably from about 10° C. to about 30° C. The molar ratio of reactants can vary. Generally, a molar ratio of cyclohex-3-en-1-ol to oxidizing agent is from about 0.8 to about 1.0. The reaction is usually conducted by forming a mixture of the alcohol and oxidizing agent, preferably while agitating the reaction mixture, e.g. by stirring, and maintaining the desired reaction temperature. The resulting product epoxy-alcohol may be purified or converted without isolation into the 2-exo-hydroxy-7-oxabicyclo[2.2.1]heptane by cyclization as described below.

The cyclization (ring closure) step surprisingly gave a high yield of product having the exo-hydroxy configuration in the resulting 7-oxabicyclo[2.2.1]heptan-2-ol. Many acids will catalyze this reaction, but a relatively strong acid such as sulfuric or sulfonic acids are suitable. Preferably, the acid is methanesulfonic acid or an arylsulfonic acid, such as p-toluenesulfonic, benzenesulfonic acids, or the like. Of these, p-toluenesulfonic acid is preferred. The reaction is suitably conducted by adding the acid to the epoxy-alcohol contained in an inert solvent of the type previously described for use in the preparation of the epoxy-alcohol. The reaction is conducted at a temperature conveniently in the range of from about 0° C. to about 50° C. or slightly above. Generally, the temperature is from about 5° C. to about 40° C., preferably from about 10° to about 30° C. The molar ratio of reactants can vary. Generally, the molar ratio of acid to epoxy-alcohol is from about 0.01 to about 0.10, and preferably from about 0.02 to about 0.04.

Thus, a 1,4-disubstituted-3-cyclohexen-1-ol is converted mainly to 2-exo-hydroxy-1,4-disubstituted-7-oxabicyclo[2.2.1]heptane by treating it with an oxidizing agent, such as tert-butyl hydroperoxide, or m-chloroperbenzoic acid, and then a strong acid, such as p-toluenesulfonic acid. Especially useful for obtaining a 2-exo-hydroxy-1,4-disubstituted-7-oxabicyclo[2.2.1-]heptane is treatment of the corresponding 3-cyclohexen-1-ol with tert-butyl hydroperoxide and vanadium-(IV) bis(2,4-pentanedionate) oxide as catalyst in methylene chloride followed by treatment of the intermediate epoxide, preferably in situ, with a sulfonic acid, particularly p-toluenesulfonic acid. Also, acid present during the epoxidation step produces the desired product.

The epoxidation-cyclization is disclosed and claimed in co-pending U.S. patent application Ser. No. 331,095, filed Dec. 16, 1981, and Ser. No. 414,548, filed Sept. 8, 1982, both abandoned and in Ser. No. 559,512, filed Dec. 8, 1983.

In situations where the endo form is desired, it can be obtained by oxidation of the 2-exo-hydroxy compound to the corresponding ketone followed by reduction of the ketone with sodium borohydride.

The 3-cyclohexen-1-ols useful for the preparation of Compound I can also be synthesized as described below.

Preparation of 3-cyclohexen-1-ols can be effected from p-substituted phenols in which the substituent group corresponds to methyl in the formula I of the invention by procedures of the literature for the Birch-type reduction of derivatives of benzene, many of which are detailed in Rodd's Chemistry of Carbon Compounds, Second Edition, Vol. II, Part B, pages 1–4 (1968). In an example, para-cresol is first methylated to protect the hydroxy group yielding the corresponding 4-methylanisole. This anisole is treated with a reducing agent such as lithium-ammonia or sodium-ammonia and the resulting product is hydrolyzed to yield the corresponding 4-substituted-3-cyclohexen-1-one. Treatment of this ketone with an appropriate organometallic (Grignard) reagent, QMgBr or QLi in which Q corresponds to 1-alkenyl, e.g. at 20°–60° C. in the presence of anhydrous ethers, yields the desired 1,4-disubstituted-3-cyclohexen-1-ol intermediate.

The intermediate compounds where Z is acetyl are prepared by treating the 4-isopropenyl compound, e.g. with osmium tetroxide in t-butanol followed by sodium metaperoxidate.

Where Z is —CO$_2$R, —CON(R)$_2$, —CN, in which R is H or lower alkyl, the 3-cyclohexen-1-ols can be prepared starting from suitable Diels-Alder adducts. For example, methyl pyruvate is converted by known procedures to its enol acetate and the latter is treated with isoprene to produce a Diels-Alder adduct. Hydrolysis of the acetate function affords 1-hydroxy-4-methyl-3-cyclohexene-1-carboxylic acid methyl ester, which can be converted to compounds of the invention by the epoxidation-cyclization and aralkylation procedures described above. Treatment of compounds of the invention where Z in I is methoxycarbonyl with ammonia, or dialkylamine, gives the —CON(R)$_2$ compound where R=H, or alkyl, respectively, and dehydration of the former with thionyl chloride affords the compound of the invention where Z is cyano. The ether compounds where Z is acetyl are converted to ether compounds wherein Z is —C(O)OH by treatment with potassium hypochlorite. Treatment of this acid first with SOCl$_2$ and with ammonia affords the intermediate compounds where Z is —C(O)NH$_2$.

The materials of formula I that have the R$^2$CH$_2$O group exo (formula Ia below) with respect to the oxygen-containing bridge are usually more herbicidally active than the endo form (formula Ib below) or the exo-endo mixture and are preferred.

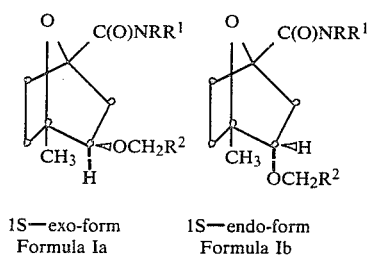

1S—exo-form  1S—endo-form
Formula Ia  Formula Ib

The compounds of formula Ia and Ib have the 1S absolute configuration shown above. Such compounds of the subclass of formula Ia of the invention that correspond in configuration are preferred.

When an isomer or a mixture of isomers other than racemic mixtures is used substantially free of all other possible isomers, they are usually at least about 70% pure, although a purity above about 80% is preferable and a purity above about 95% is highly desirable. This invention contemplates all of the herbicidally active isomers, as well as any mixtures of isomers resulting from the synthesis methods used, and deliberately created mixtures.

In another embodiment of the invention, the intermediate compounds of formula 1, wherein X is —C(CH$_3$)$_2$— and Y is —CH$_2$—, having the formula II

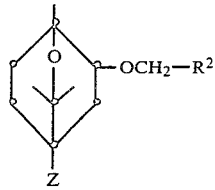

wherein Z is a cyano group, can be prepared from 4-cyano-2-oxabicyclo[2.2.1]heptan-6-ols, made from Diels-Alder adducts of suitably substituted butadienes and dienophiles containing an oxygen function, as illustrated below. Conversion to the ether of formula II of the Invention follows the earlier described procedures with retention of configuration.

Diels-Alder adducts are formed from suitable, readily available dienophiles including an acrylate ester, acrolein, methacrolein, methyl vinyl ketone, allyl alcohol, a crotonate ester and the like. The diene component is isoprene. For example, the Diels-Alder adducts IIa are prepared by treating a diene corresponding to the portion of the compound of formula IIa above the dotted line

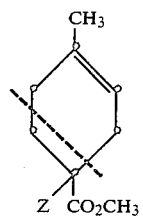

with a dienophile corresponding to the portion of the compound of formula IIa below the dotted line. Many such reactions are detailed in Rodd's Chemistry of Carbon Compounds, Second Edition, Vol II, Part B, pages 5–6 (1968). Treatment of IIa with the appropriate Grignard reagent (e.g. methyl magnesium bromide, ethyl magnesium bromide or the like) gives an alpha,alpha,4-trimethylcyclohexene-1-methanol of formula IIb below.

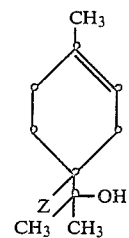

Alcohol IIb is oxidized, for example, with a peroxide, such as hydrogen peroxide or m-chloroperbenzoic acid, in a suitable solvent, such as methylene chloride, preferably in the presence of a strong acid, to yield a major amount of 1,3,3-trialkyl-2-oxabicyclo[2.2.2]octan-6-exo-ol. This exo form can be converted, if desired, into an endo-rich or substantially pure endo form. First, oxidation to the corresponding ketone, 1,3,3-trialkyl-2-oxabicyclo[2.2.2]octan-6-one, is effected with a suitable oxidizing agent, e.g. N-bromoacetamide in aqueous acetone at 5° C. or with oxalyl chloride and dimethyl sulfoxide in methylene chloride followed by addition of triethylamine. Then, the resulting ketone is converted into the endo-alcohol by reduction. For example, the ketone in a mixture of dimethoxyethane and tert-butanol is treated with sodium borohydride. Classical resolution can be applied to the 1,3,3-trialkyl-2-oxabicyclo[2.2.2]-octan-6-ols to give substantially pure individual optical forms.

The 1,3,3-trialkyl-2-oxabicyclo[2.2.2]octan-6-ols are converted into the desired ethers of the Invention, with retention of configuration, by treatment with a halide or sulfonate, $R^2CH_2X$, in which X is a halogen atom or hydrocarbylsulfonyloxy group, such as chlorine, mesyl or tolyl and the like. This reaction is carried out, preferably in the presence of a base, such as sodium hydride, and, if desired, an inert solvent, such as N,N-dimethylacetamide, N,N-dimethylformamide, benzene, toluene or the like. The compounds of the invention can be recovered and purified by conventional techniques.

The materials of formula II that have the $R^2CH_2O$ group endo (formula IIc below) are usually more herbicidally active than the exo form (formula IIc below) or the endo-exo mixture and are preferred.

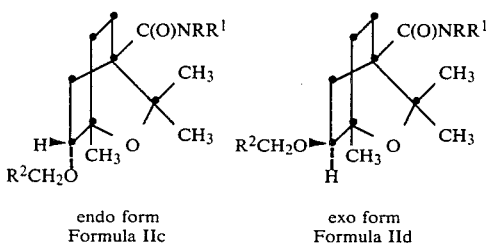

endo form
Formula IIc exo form
Formula IId

The compounds of formula IIc and IId have the 1S absolute configuration shown above. Such compounds of the subclass of formula IIc of the invention that correspond in configuration are preferred. When an isomer or a mixture of isomers other than a racemic mixture is used substantially free of all other possible isomers, they are usually about 70% pure, although a purity above about 80% is preferable and a purity above about 95% is highly desirable. This invention contemplates all of the herbicidally active isomers, as well as any mixtures resulting from the synthesis methods used, and deliberately created mixtures.

In a further embodiment of the invention, the intermediate compounds of formula 1, wherein X is —C(CH₃)₂— and Y is a single bond having the formula III

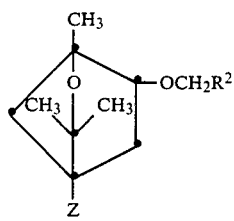

wherein Z is —CN, C(O)Hal or C(O)Y in which Y is OR or NR₂ in which R is previously defined are novel and are prepared as follows:

The 4-cyano compounds can be prepared by condensation of 1,4-dibromo-2-methyl-2-butene with an alkyl cyanoacetate or the like in the presence of base, followed by thermolysis of the 2-isopropenyl 1-cyanocyclopropanecarboxylate intermediate to a cyclopentene carboxylate. Treatment of the resulting cyano ester with a Grignard reagent, methyl magnesium bromide, yields the corresponding 1-(1-hydroxy-1-methylethyl)-3-methyl-3-cyclopentene-1-carbonitrile. This alcohol is epoxidized and cyclized to an exo-2-oxabicyclo[2.2.1]heptan-6-ol. This exo-alcohol can be oxidized to the corresponding ketone followed by reduction to a corresponding endo-2-oxabicyclo[2.2.1]heptan-6-ol as described for the compounds of formula II above.

The 4-cyano alcohol and ketone intermediates of the formula IIIa

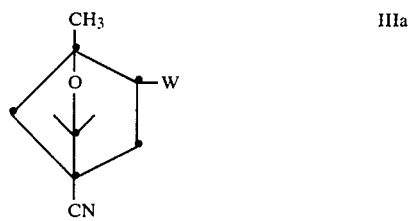

wherein W is —OH or =O are novel, per se, and are important intermediates to the novel ethers where Z is —CN, CO₂R or

in which each R is H or a hydrocarbyl group, e.g. alkyl of 1 to 4 carbon atoms. The alcohol of formula IIIa is treated with $R^2CH_2X$, e.g. a benzylic or tetrahydro-2-pyranylmethyl halide or hydrocarbylsulfonate to yield the desired intermediate ether III.

The 4-cyano compound (alcohol or ether) is converted to the 4-carboxamide compounds by methods similar to those previously described for the compounds of formula I and by conventional methods of converting nitriles to amides, e.g. by treatment with a peroxy compound, such as hydrogen peroxide, and strong base, such as alkali metal hydroxide, preferably in the presence of a solvent.

The 4-carboxamide compound is converted to the acid where Z is —C(O)OH by conventional methods using a base such as potassium hydroxide in the presence of ethylene glycol.

The 4-carboxylic acid compound is converted to the ester where Z is —C(O)OR¹ by treatment with the corresponding alkanol in the presence of a suitable coupling system, such as dicyclohexylcarbodiimide and 4-dimethylaminopyridine, in the presence of an inert solvent, such as diethyl ether.

The compounds of formulas III and IIIa are claimed in concurrently filed U.S. patent application, Ser. No. 621,013, filed June 15, 1984. This application also claims the 3-(1-hydroxy-1-methylethyl)-1-methyl-6-oxabicyclo[3.1.0]hexane-3-carbonitriles, the preparation of which is discussed above.

The materials of formula III that have the $R^2CH_2O$ group endo (formula IIIc below) are usually more herbicidally active than the exo form (formula IIIb below) or the endo-exo mixture and are preferred.

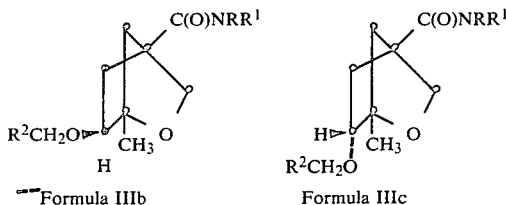

Formula IIIb          Formula IIIc

These compounds of formula IIIb and IIIc have the 1S absolute configuration shown above. The compounds of the formula IIIc of the invention are preferred. When an isomer or a mixture of isomers other than a racemic mixture is used substantially free of all other possible isomers, they are usually about 70% pure, although purity above 80% is preferred and a purity above about 95% is highly desireable. This invention contemplates all of the herbicidally active isomers, as well as any mixtures resulting from the synthesis methods used, and deliberately created mixtures.

The ether compounds of formula III wherein Z is —C(O)Hal are intermediates to the compounds of formula III where Z is —C(O)Y in which Y is OR in which R is a hydrogen atom or an alkyl group. The conversion of the ether compounds wherein Z is —C(O)Hal to those where Z is —C(O)Y is accomplished by conventional methods known in the art for preparing acids and esters from acid halides, e.g. by hydrolysis or reaction with alcohols, respectively. The compounds of formula III wherein Z is —C(O)Hal are also direct intermediates to certain of the compounds of formula 1 of the invention as discussed above.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

Methyl 1-cyano-2-(1-methylethenyl)cyclopropane-1-carboxylate

A mixture of 65.3 g of methyl cyanoacetate, 228 g of freshly pulverized potassium carbonate and 800 ml of anhydrous tetrahydrofuran was heated at reflux under nitrogen for 2 hours. A solution of 150.5 g of 1,4-dibromo-2-methyl-2-butene in 500 ml of anhydrous tetrahydrofuran was added slowly dropwise to the refluxing reaction mixture over a period of two days. The solids were removed from the cooled reaction mixture by filtration through a bed of celite. The filtrate was concentrated in vacuo to leave 111.4 g of yellow oil. Distillation of the oil gave 81.3 g of the desired product as a colorless oil: b.p. 95°–105° C. (0.05 mm Hg) consisting of two isomers in a ratio of 2:1 by GLC.

EMBODIMENT 2

Methyl 1-cyano-3-methylcyclopent-3-ene-1-carboxylate

A solution of 41.0 g of methyl 1-cyano-2-(1-methylethenyl)cyclopropane-1-carboxylate in 300 ml of toluene was passed through a pyrolysis column packed with glass helices and held at 425° C. A nitrogen flow rate was chosen which resulted in a contact time of 1–2 sec and the pyrolysate was collected in a dry ice-isopropyl alcohol cooled flask. The toluene solution was washed with 300 ml of saturated aqueous sodium bicarbonate and 300 ml of saturated sodium chloride solution, dried ($MgSO_4$), and concentrated in vacuo to leave 32.5 g of brown oil. Distillation of the oil gave 30.4 g of the desired product as a yellow oil: b.p. 75°–100° (0.05 mm Hg).

EMBODIMENT 3

1-(1-Hydroxy-1-methylethyl)-3-methyl-3-cyclopentene-1-carbonitrile

Under nitrogen, a solution of 33.2 g of methyl 1-cyano-3-methylcyanopent-3-ene-1-carboxylate in 300 ml of anhydrous tetrahydrofuran was added dropwise over 30 minutes to a solution of 167 ml of a 3M solution of methylmagnesium bromide in diethyl ether in 200 ml of anhydrous tetrahydrofuran. During the addition, the temperature was controlled at 15° C. by an ice-water bath. After being stirred at room temperature for 16 hours, the reaction mixture was diluted with 1000 ml of diethyl ether and poured into 400 ml of cold, saturated, aqueous ammonium chloride solution. After the phases were separated, the organic layer was washed with 400 ml of water and 400 ml of saturated sodium chloride solution, dried ($MgSO_4$), and concentrated in vacuo or leave 36.7 g of orange oil. Kugelrohr distillation gave 27.7 g of the desired product as an orange oil: b.p. 77° C. (0.02 mm Hg).

EMBODIMENT 4

3-(1-Hydroxy-1-methylethyl)-1-methyl-6-oxabicyclo[3.1.0]hexane-3-carbonitrile, (1α,3α,5α)isomer and (1α,3β,5α)isomer To a stirred mixture of 11.65 g of 1-(1-hydroxy-1-methylethyl)-3-methyl-3-cyclopentene-1-carbonitrile in 700 ml of methylene chloride and 210 ml of aqueous sodium bicarbonate was added portionwise at 25°–35° C. 15.3 g of 85% m-chloroperbenzoic acid. After stirring overnight, the phases were separated and the organic phase was washed successively with 200 ml of 1N sodium hydroxide, 200 ml of water and 200 ml of saturated aqueous sodium chloride, dried ($MgSO_4$), and concentrated in vacuo to leave 14.2 g of a colorless oil, as a 1.2;1.0 mixture of diastereomeric epoxides. These diastereomers were separated by flash silica gel column chromatography using 2:8:40 tetrahydrofuran/ethyl acetate/hexane as eluent to give 5.1 g of the less polar (1α,3β,5α) isomer as a colorless oil and using 2:15:33 ratio of the same solvents to give 5.4 g of the more polar (1α,3α,5α)isomer as a colorless oil.

EMBODIMENT 5

6-exo-Hydroxy-1,3,3-trimethyl-2-oxabicyclo[2.2.1]heptane-4-carbonitrile

A solution of 5.30 g of 3-(1-hydroxy-1-methylethyl)-1-methyl-6-oxabicyclo[3.1.0]hexane-3-carbonitrile (1α,-

3α,5α) and 0.37 g of anhydrous p-toluenesulfonic acid in 50 ml of chloroform was stirred at room temperature for 48 hours. After dilution with 100 ml of methylene chloride, the solution was washed with 50 ml of 25% aqueous potassium carbonate, 50 ml of water and 50 ml of saturated aqueous sodium chloride, dried (MgSO$_4$), and concentrated in vacuo to provide 4.9 g of the desired product as a cream-colored solid, m.p. 94°–98° C.

EMBODIMENT 6

1,3,3-trimethyl-6-oxo-2-oxabicyclo[2.2.1]heptane-4-carbonitrile

A 100 ml roundbottom flask was charged with 50 ml of methylene chloride and 2.4 g of oxalyl chloride. The solution was cooled to −60° C. and a solution of 3.0 g of dimethyl sulfoxide in 6 ml of methylene chloride was added dropwise. The reaction mixture was stirred for 10 minutes at −60° C. and then a solution of 2.90 g of exo-6-hydroxy-1,3,3-trimethyl-2-oxabicyclo[2.2.1]heptane-4-carbonitrile in 3.3 ml of methylene chloride was added dropwise. A white precipitate formed during the addition. The reaction mixture was stirred at −60° C. for 15 minutes and then was allowed to warm to −20° C. Then 8.80 g of triethylamine was added rapidly dropwise by syringe. After stirring for 10 minutes, 50 ml of water was added and the resulting phases were separated. The aqueous phase was extracted twice with 30 ml of methylene chloride and the combined extracts were washed with 60 ml of water and 60 ml of saturated sodium chloride, dried (MgSO$_4$) and concentrated in vacuo to leave 3.07 g of a semi-solid amber residue. This residue was flash chromatographed on silica gel using 4:16:80 tetrahydrofuran/ethyl acetate/hexane as eluent to give two fractions. The first fraction of 1.85 g of cream-colored solid was recrystallized using 1:5-diethyl ether/hexane as a solvent to give 1.13 g of the desired product: m.p. 74°–76° C.

EMBODIMENT 7

6-endo-Hydroxy-1,3,3-trimethyl-2-oxabicyclo[2.2.1]heptane-4-carbonitrile

A 25 ml, three-necked roundbottom flask was flushed with nitrogen, sealed and charged with 7.3 ml of a 1.0M solution of L-selectride (LiBH(sec-butyl)$_3$) in tetrahydrofuran. The solution was cooled to −70° C., becoming opaque white. A solution of 1.10 g of 1,3,3-trimethyl-6-oxo-2-oxabicyclo[2.2.1]heptane-4-carbonitrile in 3 ml of anhydrous tetrahydrofuran was added dropwise. The addition was very exothermic. The reaction mixture was stirred at −70° C. for 1 hour, followed by room temperature for an additional hour. Then, successively were added (a) 0.80 ml of water, (b) 1.60 ml of ethanol, and with ice-bath cooling, (c) 5.88 ml of 10% sodium hydroxide, and (d) 2.49 g of 30% hydrogen peroxide. The reaction mixture was stirred 1 hour at room temperature and then saturated with solid potassium carbonate. The mixture was diluted with 30 ml of 1:1 diethyl ether/tetrahydrofuran solution and 7 ml of water. The phases were separated and the aqueous phase was extracted four times with 30 ml portions of 1:1 tetrahydrofuran/diethyl ether. The combined organic phases were washed twice with 40 ml of saturated sodium chloride, dried (MgSO$_4$) and stripped in vacuo to leave 1.07 g of a cream-colored solid m.p. 68°–83° C. The solid was recrystallized from 1:5 diethyl ether/hexane to give 790 mg of the desired product, m.p. 85°–88° C.

EMBODIMENT 8

1,3,3-Trimethyl-6-endo-(phenylmethoxy)-2-oxabicyclo[2.2.1]heptane-4-carbonitrile A 200 ml three-necked flask was charged with 3.62 g of 50% sodium hydride and 20 ml of dimethylformamide and flushed with nitrogen. A solution of 7.36 of endo-6-hydroxy-1,3,3-trimethyl-2-oxabicyclo[2.2.1]heptane-4-carbonitrile in 40 ml of dimethylformamide was added dropwise while cooling to 25° C. using an ice bath. The resulting grey opaque solution was stirred for 2½ hours, turning green. To this mixture was added dropwise 11.80 g of benzyl bromide in 30 ml of dimethylformamide at 25° C. The reaction mixture was stirred at room temperature overnight. The resulting mixture was quenched with 500 ml of water and extracted thrice with 300 ml of methylene chloride. The combined organic extracts were washed with 300 ml of water and 300 ml of saturated sodium chloride solution, dried (MgSO$_4$) and stripped in vacuo to leave 12.72 g of a damp brown solid. This solid was flashed chromatographed on silica gel using 1.5:3.8 diethyl ether/hexane solvent to give 7.44 g of a cream-colored solid, m.p. 66°–80° C., which was recrystallized using 1:6 diethyl ether/hexane as solvent to yield 5.95 g of the desired product as a white solid, m.p. 84°–88° C.

EMBODIMENT 9

1,3,3-Trimethyl-6-endo-(phenylmethoxy)-2-oxabicyclo[2.2.1]heptane-4-carboxamide

A 25 ml three-necked roundbottom flask was charged with 2.71 g of 1,3,3-trimethyl-6-endo-(phenylmethoxy)-2-oxabicyclo[2.2.1]heptane-4-carbonitrile and 7.5 ml of methylene chloride. This solution was cooled to 0° C. before the sequential addition of 7.5 ml of 30% hydrogen peroxide, 0.697 g of tetrabutylammonium sulfate and 5.0 ml of 20% sodium hydroxide solution. The resulting biphasic mixture was allowed to warm to room temperature and was stirred vigorously for two days. The resulting mixture was diluted with 30 ml of methylene chloride. The separated organic phase was washed twice with 30 ml of saturated sodium chloride solution, dried (MgSO$_4$), and stripped in vacuo to leave 3.36 g of a wet cream-colored solid, m.p. 131°–145° C. This solid was combined with similar material from a second experiment and the combined solids were flashed chromatographed on silica gel using 1:1:2 tetrahydrofuran/ethyl acetate/hexane as solvent to give 3.17 g of a white solid. A 1.78 g portion of this solid was recrystallized using 2:1:~5 diethyl ether/tetrahydrofuran/hexane as solvent to give 1.60 g of the desired product as white crystals, m.p. 151.5°–152° C.

EMBODIMENT 10

1,3,3-trimethyl-6-endo-(phenylmethoxy)-2-oxabicyclo[2.2.1]heptane-4-carboxylic Acid To a mixture of 1.056 g of 1,3,3-trimethyl-6-endo-(phenylmethoxy)-2-oxabicyclo[2.2.1]heptane-4-carboxamide in 40 ml of ethylene glycol were added 6.0 g of freshly pulverized solid potassium hydroxide. The resulting mixture was heated at reflux for seven hours to give a yellow solution. This solution was diluted with 300 ml of water, acidified to pH of 1 with cold 3N hydrochloric acid and extracted thrice with 150 ml portions of methylene chloride. The combined methylene chloride extracts were washed with 150 ml of water and with 150 ml of saturated sodium chloride solution, dried (MgSO$_4$) and stripped in vacuo to leave 1.45 g of a cream-colored solid. This was combined with 1.4 g of similar material from a second experiment and the combined solids were recrystallized using 1:1 diethyl ether/hexane as solvent to give 710 mg of the desired product as a white solid, m.p. 171°–172° C.

EMBODIMENT 11

1,3,3-Trimethyl-6-endo-(phenylmethoxy)-2-oxabicyclo[2.2.1]heptane-4-carbonyl Isocyanate To a solution of 0.42 g of 1,3,3-trimethyl-6-endo-(phenylmethoxy)-2-oxabicyclo[2.2.1]heptane-4-carboxamide in 4 ml of 1,2-dichloroethane was added via syringe 0.222 g of oxalyl chloride. Gas evolved immediately, and the resulting solution was stirred at room temperature for 1 hour. The solution was heated at 50° C., resulting in gas evolution and vigorous reaction to a temperature of 65° C. After 10 minutes, the solvent was stripped to leave 0.38 g of the desired product as an orange oil.

EMBODIMENT 12

1,3,3-Trimethyl-N-(methylaminocarbonyl)-6-endo-(phenylmethoxy)-2-oxabicyclo[2.2.1]heptane-4-carboxamide To a solution of 0.63 g of 1,3,3-trimethyl-6-endo-(phenylmethoxy)-2-oxabicyclo[2.2.1]heptane-4-carbonyl isocyanate in 10 ml of methylene chloride under nitrogen was added 0.40 g of monomethylamine by bubbling at −25° C. The reaction was very exothermic. The resulting mixture was stirred at −20° C. for ½ hour and then at room temperature for 2 hours. The solvents were stripped to leave 0.60 g of a whitish solid, which was flash chromatographed on silica gel using 1:1 ethyl acetate/hexane as solvent to give 520 mg of a white solid. This solid was triturated with hexane to yield 450 mg of the desired product as a white solid: m.p. 164°–165° C.

EMBODIMENTS 13–18

Following procedures similar to those described in Embodiment 12 above, materials were prepared as set forth in Table I, below.

TABLE I endo-2-OXABICYCLO[2.2.1]HEPTANE ETHERS

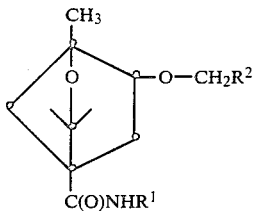

| Embodiment | R$^1$ | R$^2$ |
|---|---|---|
| 13 | C(O)NHphenyl | phenyl |
| 14 | C(O)NHCH$_2$CH=CH$_2$ | phenyl |
| 15 | C(O)NH(3,4-dichlorophenyl) | phenyl |
| 16 | C(O)NHCH$_2$C≡CH | phenyl |
| 17 | C(O)NHisopropyl | phenyl |
| 18 | C(O)N(CH$_3$)$_2$ | phenyl |

EMBODIMENT 19

1,3,3-Trimethyl-6-endo-(phenylmethoxy)-2-oxabicyclo[2.2.1]heptane-4-carbonyl Chloride To a 50 ml roundbottom flask containing 1.15 g of 1,3,3-trimethyl-6-endo-(phenylmethoxy)-2-oxabicyclo[2.2.1]heptane-4-carboxylic acid and 15 ml of 1,2-dichloroethane was added via syringe 0.43 ml of oxalyl chloride. The resulting solution was heated at 55°–60° C. for 3 hours. The solvent was stripped under vacuo to leave the desired product as an orange oil.

EMBODIMENT 20

1,3,3-Trimethyl-N-(methylsulfonyl)-6-endo-(phenylmethoxy)-2-oxabicyclo[2.2.1]heptane-4-carboxamide A 15 ml three-necked flask was charged with 0.15 g of 50% sodium hydride in 5 ml of dimethylformamide carefully followed by 0.27 g of methanesulfonamide. Some foaming occurred. The resulting mixture was stirred for 2 hours at room temperature and then heated to 80° C. for 2 hours. A solution of 0.75 g of 1,3,3-trimethyl-6-endo-(phenylmethoxy)-2-oxabicyclo[2.2.1]heptane-4-carbonyl chloride in 5 ml of dimethylformamide was added dropwise and the mixture was stirred at room temperature for 20 hours. Then another 0.15 g of 50% sodium hydride in 5 ml of dimethylformamide was prepared and the crude reaction mixture was added to it (some foaming). The resulting mixture was stirred at room temperature overnight. The solvent was stripped under vacuo leaving a cream-colored residue. The residue was dissolved in 100 ml of a 1:1 water/methylene chloride solution. The aqueous layer was acidified to pH 2 with 1N hydrochloric acid, extracted twice with 50 ml of methylene chloride. The combined organic phases was washed with 100 ml of water and 100 ml of saturated sodium chloride solution, dried (MgSO$_4$) and stripped under vacuo to leave 1.06 g of a thick colorless oil. The oil was combined with similar material from another experiment, and the combined material was flash chromatographed on silica gel using 1:4 hexane/tetrahydrofuran as solvent to leave 0.90 g of a thick colorless oil. This oil was dissolved in 40 ml of diethyl ether, washed twice with 30 ml of saturated sodium sulfite, dried (MgSO$_4$) and stripped to leave 0.75 g of a thick, colorless oil. The oil was dissolved in methylene chloride and fractionated on a Florisil column. Graduated elution starting at 100% methylene chloride and ending with a 4:1 methylene chloride/methanol afforded 0.44 g of an opaque whitish oil-glass. This material was crystallized from 1:4:0.1 diethyl ether/hexane/methylene chloride solution to give 0.12 g of the desired product as a cream-colored solid, m.p. 96°–100° C.

EMBODIMENT 21

N-(Ethoxycarbonyl)-1,3,3-trimethyl-6-endo-(phenylmethoxy)-2-oxabicyclo[2.2.1]heptane-4-carboxamide A 15 ml three-necked roundbottom flask was charged with 0.29 g of 50% sodium hydride in 3 ml of tetrahydrofuran and flushed with nitrogen. A solution of 1.45 g of 1,3,3-trimethyl-6-endo-(phenylmethoxy)-2-oxabicyclo[2.2.1]heptane-4-carboxamide in 8 ml of tetrahydrofuran was added dropwise at 0° C. Gas evolved during the addition. The reaction mixture was stirred for 2 hours at room temperature. The resulting opaque white solution was cooled to 0° C. while 0.48 ml of ethyl chloroformate was added via syringe. The reaction was exothermic. The mixture was stirred overnight, and an additional 0.24 g of 50% sodium hydride in 3 ml of tetrahydrofuran was added via pipette (gas evolution). The opaque white and viscous mixture was stirred at room temperature for 4 hours, diluted with 100 ml of cold water, acidified to pH 2 with 1N hydrochloric acid and extracted thrice with 50 ml of methylene chloride. The combined methylene chloride layers was washed with 40 ml of water and 40 ml of saturated sodium chloride solution, dried (MgSO$_4$), and stripped under vacuo to leave 1.91 g of a thick colorless glass-like material. This material was flash chromatographed on silica gel using 1:1 ethyl acetate/hexane as solvent, and a single fraction was collected as 1.70 g of the desired product as a colorless oil.

EMBODIMENT 22

N-Methoxy-1,3,3-trimethyl-6-endo-(phenylmethoxy)-2-oxabicyclo[2.2.1]heptane-4-carboxamide To a solution of 0.58 g of methoxyamine, 1.90 ml of triethylamine and 10 ml of methylene chloride were added dropwise at 0° C., the acid chloride product of Embodiment 19 dissolved in 10 ml of methylene chloride. The reaction mixture was stirred at room temperature overnight, diluted with 50 ml of methylene chloride, washed with 40 ml of hydrochloric acid, 40 ml of saturated sodium bicarbonate solution, 40 ml of water, and 40 ml of saturated sodium chloride solution, dried (MgSO$_4$) and stripped in vacuo to leave 2.11 g of a thick, pale yellow oil. This oil was crystallized from 1:1 diethyl ether/hexane as solvent to give 0.90 g of the desired product as a white solid, m.p. 121.5°–124° C.

EMBODIMENT 23

N,N-diacetyl-1,3,3-trimethyl-6-endo-(phenylmethoxy)-2-oxabicyclo[2.2.1]heptane-4-carboxamide (A) and N-acetyl-1,3,3-trimethyl-6-endo-(phenylmethoxy)-2-oxabicyclo[2.2.1]heptane-4-carboxamide (B)

A 50 ml three-necked roundbottom flask was charged with 0.34 g of sodium hydride in 10 ml of tetrahydrofuran. A solution of 1.445 g of 1,3,3-trimethyl-6-endo-(phenylmethoxy)-2-oxabicyclo[2.2.1]heptane-4-carboxamide in 5 ml of tetrahydrofuran was added at 0° C. The reaction mixture was stirred at room temperature for 2 hours. Then 0.36 ml of acetyl chloride was added via syringe at 15° C. The mixture was stirred at room temperature for two days and then 0.2 g of 50% sodium hydride in 5 ml of tetrahydrofuran was added (gas evolution). The mixture was stirred overnight at room temperature, quenched with 75 ml of water, acidified to pH 6.0 with 1N hydrochloric acid and extracted thrice with 75 ml portions of methylene chloride. The combined methylene chloride layers was washed with 75 ml of water and 75 ml of saturated sodium chloride solution, dried (MgSO$_4$) and stripped under vacuo to leave 1.73 g of a thick orange syrup. This material was flash chromatographed on a silica column using 1:1 diethyl ether/hexane as solvent to give 0.60 g of the desired product (B) as a yellow oil, R$_f$(1:1 diethyl ether/hexane) of 0.18; and 0.16 g of the desired product (A) as a white glass, R$_f$(1:1 diethyl ether/hexane) of 0.06.

EMBODIMENT 24

N-(Diethoxyphosphinyl)-1,3,3-trimethyl-6-endo-(phenylmethoxy)-2-oxabicyclo[2.2.1]heptane-4-carboxamide A 50 ml three-necked flask flushed with nitrogen was charged with 0.29 g of 50% sodium hydride in 20 ml of tetrahydrofuran. A solution of 1.445 g of 1,3,3-trimethyl-6-endo-(phenylmethoxy)-2-oxabicyclo[2.2.1]heptane-4-carboxamide in 10 ml of tetrahydrofuran was added dropwise at 15°–25° C. Gas evolved for about 15 minutes thereafter. The yellow reaction mixture containing some grey solids was stirred at room temperature for 2½ hours. A solution of 0.72 ml of diethyl chlorophosphate in 2 ml of tetrahydrofuran was added dropwise via syringe at 0° to 5° C. (heat evolution). The reaction mixture was stirred for ½ hour to give a clear yellow solution, then overnight. An additional 0.25 g of 50% sodium hydride in tetrahydrofuran was added via pipette. After stirring for 2 hours, 0.50 ml of diethyl chlorophosphate was added and the mixture was again stirred overnight. Another 0.50 ml of diethyl chlorophosphate was added and the mixture was stirred for 3 hours to give a clear yellow solution. The final reaction mixture was quenched with 120 ml of cold water, diluted with 120 ml of methylene chloride, and then acidified to pH 4.0 with 1N hydrochloric acid. The phases were separated and the aqueous phase was extracted twice with 100 ml portions of methylene chloride. The combined extracts was washed with 100 ml of water and 100 ml of saturated sodium chloride, dried (MgSO$_4$) and stripped under vacuo to leave 2.32 g of a thick colorless syrup. This material was flash chromatographed on a silica gel column using 2:1:0.2 methylene chloride/hexane/methanol as a solvent to give a single fraction of 1.60 g of the desired product as a thick colorless oil.

EMBODIMENT 25

N,N'-Carbonylbis(1,3,3-trimethyl-6-endo-(phenylmethoxy)-2-oxabicyclo[2.2.1]heptane-4-carboxamide)

To a 5 ml roundbottom flask charged with 0.578 g of 1,3,3-trimethyl-6-endo-(phenylmethoxy)-2-oxabicyclo[2.2.1]heptane-4-carboxamide and 2 ml of 1,2-dichloroethane was added by syringe 0.22 ml of oxalyl chloride. The reaction mixture was stirred at 25° C. for 1½ hours with initial evolution of gas. The solvent and other volatiles were stripped in vacuo. The residue was dissolved in methylene chloride and the solvent and volatiles were again removed in vacuo. The residue was redissolved in 4 ml of 1,2-dichloroethane and 0.055 g of oxalyl chloride was added via syringe. The reaction mixture was heated at reflux for 4½ hours. The solvents were stripped in vacuo. The residue was treated twice with 30 ml of methylene chloride and stripped to leave 0.50 g of a yellow oil. The oil was dissolved in 4 ml of 1,2-dichloroethane and 0.055 g of oxalyl chloride was added. The solution was heated at reflux for 24 hours. The solvents were stripped off, the residue was extracted twice with 15 ml of methylene chloride, and the extract was stripped to leave 0.41 g of a yellow glass-like crystal. This material was purified by flash chromatography on silica gel using 12:35:53 tetrahydrofuran/ethyl acetate/hexane as solvent. One fraction of 0.25 g of a thick colorless oil was recovered. This oil was crystallized from 1:12 diethyl ether/hexane to yield 80 mg of the desired product as a white solid, m.p. 80°–81.5° C.

EMBODIMENT 26

(±)-4-Methyl-1-(1-chloro-1-methylethyl)-3-cyclohexen-1-ol

To a stirred solution of 15.2 g of 2,2,6-trimethyl-1-oxaspiro(2.5)oct-5-ene in 200 ml of diethyl ether held at −10° C. was added dropwise 32 ml of 3.8N ethereal hydrogen chloride. After one hour at 0°–5° C., the mixture was washed with three 50 ml portions of water, dried and distilled to give 14.5 g of the desired product, b.p. 70°–75° C. (0.4 mm).

EMBODIMENT 27

(±)-2-exo-(Benzyloxy)-4-(1-chloro-1-methylethyl)-1-methyl-7-oxabicyclo[2.2.1]heptane Following procedures similar to those described in Embodiments 4 and 5, (±)-4-methyl-1-(1-chloro-1-methylethyl))-3-cyclohexen-1-ol was treated with vanadium(IV) bis(2,4-pentanedionate)oxide and tert-butyl hydroperoxide followed by p-toluenesulfonic acid to obtain (±)-2-exo-hydroxy-4-(1-chloro-1-methylethyl)-1-methyl-7-oxabicyclo[2.2.1]heptane. This intermediate product was treated with benzyl chloride by procedures similar to those described in Embodiment 8 to yield the desired product, b.p. 120°–122° C. (0.15 mm).

EMBODIMENT 28

(±)-2-exo-(2-Fluorobenzyloxy)-4-(1-chloro-1-methylethyl)-1-methyl-7-oxabicyclo[2.2.1]heptane By procedures similar to Embodiment 8, (±)-2-exo-hydroxy-4-(1-chloro-1-methylethyl)-1-methyl-7-oxabicyclo[2.2.1]heptane was treated with 2-fluorobenzyl chloride to yield the desired product, b.p. 133°–134° C. (0.2 mm).

EMBODIMENT 29

(±)-2-exo-(2-Methylbenzyloxy)-4-(1-chloro-1-methylethyl)-1-methyl-7-oxabicyclo[2.2.1]heptane By procedures similar to Embodiment 8, (±)-2-exo-hydroxy-4-(1-chloro-1-methylethyl)-1-methyl-7-oxabicyclo[2.2.1]heptane was treated with 2-methylbenzyl chloride to yield the desired product, b.p. 128°–130° C. (0.1 mm).

EMBODIMENTS 30–32

The 4-(1-chloro-1-methylethyl)ether compounds of Embodiments 27, 28 and 29 were each respectively treated with 1.1 molar equivalents of sodium hydride in N,N-dimethylacetamide at 80° C. for 2 hours to give the dehydrochlorinated products set forth in Table II below.

TABLE II
EXO-7-OXABICYCLO[2.2.1]HEPTANE ETHERS

| Embodiment | $R_1$ | $R_2$ | $R_3$ | b.p., °C. (mm) |
|---|---|---|---|---|
| 30 | $CH_3$ | $C=CH_2$ / $CH_3$ | 2-$CH_3$ | 110–114 (0.1) |
| 31 | $CH_3$ | $C=CH_2$ / $CH_3$ | 2-F | 105 (0.1) |
| 32 | $CH_3$ | $C=CH_2$ / $CH_3$ | H | 110–114 (0.1) |

EMBODIMENT 33

(±)-2-exo-Benzyloxy-1-methyl-4-acetyl-7-oxabicyclo[2.2.1]heptane

To a stirred mixture of 15.1 g of the ether of Embodiment 32 above, 150 ml of ether and 150 ml of water were added 30 ml of 2% osmium tetroxide in tert-butanol. After 15 minutes, 27.2 g of sodium metaperiodate was added and the reaction was continued at reflux for 18 hours. The ether layer was separated and the aqueous layer was extracted with ether. The combined ether extracts was washed, dried, concentrated, and Claisen-distilled to give 11.1 g of the desired product, b.p. 120° C. (0.1 mm).

EMBODIMENT 34

(±)-2-exo-Benzyloxy-1-methyl-4-carboxy-7-oxabicyclo[2.2.1]heptane

To a stirred solution of 8.4 g of the ether of Embodiment 33 above in 240 ml of dioxane held at 10°–15° C. was added a solution of 6.5 ml of bromine in 160 ml of water containing 42 g of potassium hydroxide. The mixture was stirred for 18 hours at 10°–25° C. and then poured into 300 ml of one-fourth saturated sodium bisulfite. This mixture was first extracted with 300 ml of ether and then acidified with 110 ml of 6N hydrochloric acid. The acidified mixture was extracted with three 250 ml portions of ether. The combined latter extracts was washed, dried and concentrated at 40° C. and <1 mm to give 8.8 g of crude product. Recrystallization from ether-pentane gave 6.5 g of the desired product, m.p. 93°–95° C.

EMBODIMENT 35

(±)-2-exo-Benzyloxy-1-methyl-4-(aminocarbonyl)-7-oxabicyclo[2.2.1]heptane

The product of Embodiment 34 above was converted to the acid chloride and the latter was treated with ammonia to give the desired product, m.p. 122°–123° C.

EMBODIMENT 36

(±)-2-exo-Benzyloxy-1-methyl-4-cyano-7-oxabicyclo[2.2.1]heptane

The ether of Embodiment 35 above was treated with acetic anhydride and pyridine to give the desired product, recovered as an oil.

EMBODIMENTS 36-39

Following procedures similar to those described for Embodiments 18, 24 and 21, the ethers set forth in Table III below are prepared.

TABLE III
4-SUBSTITUTED 2-OXABICYCLO[2.2.2]-OCTAN-6-OL ETHERS

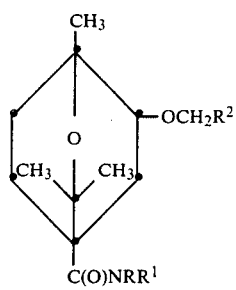

| Embodiment | R | $R^1$ | $R^2$ |
|---|---|---|---|
| 36 | H | $C(O)NHC_2H_5$ | 2-chlorophenyl |
| 37 | H | $C(O)N(C_3H_7)_2$ | 3-methyl-2-furanyl |
| 38 | H | $P(O)(OC_2H_5)_2$ | pyrazin-2-yl |
| 39 | H | $C(O)OCH_3$ | 4-fluorophenyl |
| 40 | | =C=O | phenyl |

EMBODIMENTS 41-45

Following procedures similar to those described for Embodiments 16, 21, 24 and 20 above, the ethers set forth in Table IV below are prepared.

TABLE IV
4-SUBSTITUTED 7-OXABICYCLO[2.2.1] HEPTAN-2-OL ETHERS

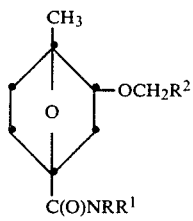

| Embodiment | R | $R^1$ | $R^2$ |
|---|---|---|---|
| 41 | H | $C(O)NH-CH_2C\equiv CH$ | phenyl |
| 42 | H | $C(O)CH_3$ | 2-methylphenyl |
| 43 | $C(O)CH_3$ | $C(O)CH_3$ | cyclohexyl |
| 44 | H | $P(O)(OCH_3)_2$ | 2-furanyl |
| 45 | H | $S(O)_2C_2H_5$ | cyclopropyl |
| 46 | | =C=O | phenyl |

EMBODIMENT 47

Tetrahydro-2-pyranylmethyl Mesylate

A stirred solution of 13.9 g of tetrahydro-2-pyranylmethanol and 18.2 g of triethylamine in 250 ml of methylene chloride was cooled to −10° C. and 15.1 g of methansulfonyl chloride was added dropwise over 5 minutes while maintaining the temperature at −10° C. to 0° C. using a cooling bath. The bath was removed and the mixture was stirred for ½ hour while the temperature reached 16° C. The reaction mixture was washed successively with 150 ml of ice water, 150 ml of 10% hydrochloric acid solution, 150 ml of saturated sodium bicarbonate solution and 150 ml of saturated sodium chloride solution, then dried (MgSO4) and evaporated under vacuum at 50° C. to give 23.7 g of a yellow oil, which was Claisen distilled to yield 19.7 g of the desired product; b.p. 110° C. (0.2 mm).

EMBODIMENT 48

6-endo-(Tetrahydro-2-pyranylmethoxy)-4-cyano-1,3,3-trimethyl-2-oxabicyclo[2.2.1]heptane A 50 ml, three-necked flask was charged with 50% sodium hydride and flushed with nitrogen. A solution of 2.54 g of 6-endo-hydroxy-4-cyano-1,3,3-trimethyl-2-oxabicyclo[2.2.1]heptane in 10 ml of dimethylformamide was added dropwise with stirring at 25° C. The reaction was exothermic and gas evolved. The reaction mixture was stirred for 2½ hours and then 3.0 g of tetrahydro-2-pyranylmethyl mesylate in 5 ml of dimethylformamide was added dropwise. The resulting mixture was stirred at room temperature for two days. An additional 0.4 g of sodium hydride was added and the reaction mixture was stirred for two days more. The resulting mixture was quenched with 150 ml of water and extracted thrice with 75 ml of methylene chloride solution, and the extract was dried (MgSO4) and stripped in vacuo to give 4.2 g of a brown oil. The oil was silica chromatographed using 1:2 ethyl acetate/hexane as eluent and the resulting first peak was silica chromatographed using 1:2:1 ethyl acetate/hexane/diethyl ether as eluent. The resulting first peak was flashed on a silica column using 1:1:2 diethyl ether/ethyl acetate/hexane as eluent. The resulting product of the first peak was crystallized from diethyl ether/hexane 1:10 as solvent to give 880 mg of the desired product as a white solid; m.p. 58.5°-62° C.

EMBODIMENT 49

6-endo-(Tetrahydro-2-pyranylmethoxy)-4-(aminocarbonyl)-1,3,3-trimethyl-2-oxabicyclo[2.2.1]heptane To a stirred solution of 1.30 g of 6-endo-(tetrahydro-2-pyranylmethoxy)-4-cyano-1,3,3-trimethyl-2-oxabicyclo[2.2.1]heptane in 7 ml of methylene chloride was added successively 5.36 g of 30% hydrogen peroxide, 0.32 g of tetrabutylammonium sulfate and 2.35 g of 20% sodium hydroxide. The reaction mixture was stirred overnight at room temperature. An additional 2.0 g of 30% hydrogen peroxide was added and the mixture was stirred again overnight. The resulting mixture was diluted with 20 ml of methylene chloride. The resulting methylene chloride phase was washed with 15 ml of saturated sodium chloride, dried (MgSO4) and stripped under vacuo to leave 1.46 g of a thick yellow oil, which crystallized after sitting at room temperature for a day. The solid was recrystallized from 1:8 ethyl acetate/hexane as a slovent to give 1.20 g of solid, which was recrystallized using 1:5 ethyl acetate/hexane to give 1.08 g of the desired product; m.p. 175°-205° C. (with decomposition).

The compounds of the Invention have been found useful for influencing plant growth and controlling the growth of unwanted plants, being particularly active with respect to grassy weeds and some broadleafed plants. For example, the compounds can change plant morphology; depress the growth of plants, such as broadleafed weeds; inhibit germination; or totally or selectively kill plants depending on the amount used. As herbicides, they appear to be more effective when applied preemergence or pre-plant incorporated (applied to the soil before the seeds have sprouted) than when applied postemergence (applied to the foliage). However, the compounds of the Invention show improved broadleaf activity and postemergence activity, particularly on grasses.

Protection of a locus or area from undesireable plants is effected by applying a Compound of the Invention, ordinarily a composition of one of the aforementioned types, to the soil in which the plant is growing or in which the seeds are present or to plant and foliage. The Compounds of the Invention, of course, are applied in amounts sufficient to exert the desired action.

For application, the compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula 1.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration of impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluable; certain organic solids or inorganic salts may be disolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and 1-3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula 1, ordinarily in a composition of one of the aforementioned types, to soil in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected from 0.1 to 10.0 kg per hectare of the compound of Formula 1 will be satisfactory.

EXAMPLES OF ACTIVITY WITH RESPECT TO PLANTS

In the following examples, the species of plants that were tested were:

Barnyardgrass (watercress)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnson grass—*Sorghum halepense*
Morningglory—*Ipomoea purpurea* L. (Roth)

TEST PROCEDURES

The preemergence (soil) herbicidal activity of compounds of Formula 1 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula 1 was eveluated by spraying 10-day-old large crabgrass plants, 13-day-old pigweed plants, 6-day-old Johnsongrass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

Results of the preemergence and postemergence herbicidal activity tests are set forth in Table V.

TABLE V

| | HERBICIDAL ACTIVITY | | | | | | | | | | | | | |
| --- | --- | --- | --- | --- | --- | --- | --- | --- | --- | --- | --- | --- | --- | --- |
| | Preemergence | | | | | | | Postemergence | | | | | | |
| Compound | Barn-yard-grass | Garden Cress | Downy Brome | Velvet-leaf | Yellow Foxtail | Sickle-pod | Morn-ing-glory | Crab-grass | Pig-weed | Johnson-grass | Velvet-leaf | Yellow Foxtail | Sickle-pod | Morn-ing-glory |
| 13 | 8 | 7 | 7 | 2 | 7 | 2 | — | 4 | 5 | 2 | 2 | 5 | 6 | — |
| 12 | 9 | 7 | 9 | 7 | 8 | 7 | — | 4 | 4 | 2 | 5 | 3 | 5 | — |
| 14 | 9 | 7 | 9 | 7 | 8 | 7 | — | 6 | 6 | 2 | 4 | 2 | 4 | — |
| 20 | 9 | 5 | 4 | 3 | 2 | — | 0 | 3 | 5 | 0 | 5 | 0 | — | 2 |
| 26 | 9 | 7 | 7 | 3 | 7 | — | 2 | 5 | 5 | 3 | 6 | 0 | — | 3 |
| 15 | 7 | 2 | 5 | 0 | 0 | — | 0 | 4 | 4 | 2 | 6 | 6 | — | 2 |
| 16 | 9 | 7 | 9 | 7 | 8 | — | 6 | 4 | 4 | 2 | 5 | 2 | — | 2 |
| 17 | 9 | 7 | 9 | 7 | 8 | — | 5 | 6 | 3 | 2 | 7 | 5 | — | 3 |

TABLE V-continued

| | HERBICIDAL ACTIVITY | | | | | | | | | | | | |
|---|---|---|---|---|---|---|---|---|---|---|---|---|
| | Preemergence | | | | | | Postemergence | | | | | | |
| Compound | Barnyard-grass | Garden Cress | Downy Brome | Velvet-leaf | Yellow Foxtail | Sickle-pod | Morning-glory | Crab-grass | Pig-weed | Johnson-grass | Velvet-leaf | Yellow Foxtail | Sickle-pod | Morning-glory |
| 21 | 9 | 7 | 9 | 6 | 8 | — | 5 | 4 | 4 | 2 | 3 | 2 | — | 3 |
| 24A | 9 | 7 | 9 | 7 | 8 | — | 7 | 3 | 4 | 0 | 4 | 2 | — | 5 |
| 24B | 9 | 7 | 9 | 7 | 8 | — | 7 | 7 | 7 | 3 | 7 | 2 | — | 6 |
| 23 | 9 | 7 | 9 | 7 | 8 | — | 3 | 3 | 4 | 1 | 5 | 1 | — | 4 |
| 18 | 9 | 7 | 8 | 6 | 8 | — | 3 | 4 | 5 | 2 | 6 | 2 | — | 3 |
| 25 | 9 | 3 | 8 | 3 | 7 | — | 2 | 3 | 3 | 2 | 5 | 2 | — | 3 |

What is claimed is:

1. A compound of the formula

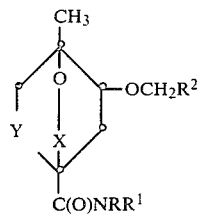

wherein R is H or —C(O)$R^3$ in which $R^3$ is a hydrogen atom; an alkyl group containing 1 to 6 carbon atoms; $R^1$ is

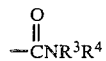

in which $R^3$ is a hydrogen atom, an alkyl group containing 1 to 6 carbon atoms or an alkenyl or alkynyl group containing 3 or 4 carbon atoms and $R^4$ is a hydrogen atom or an alkyl group containing from 1 to 6 carbon atoms, —$SO_2R^3$ in which $R^3$ has the above meaning, —P(O)(Z$R^3$)$_2$ in which Z is O, N or S and $R^3$ has the above meaning, —C(O)$R^3$ in which $R^3$ has the above meaning; —O$R^3$ in which $R^3$ has the above meaning; —C—O$R^3$ in which $R^3$ has the above meaning; (1,3,3-trimethyl-6-(phenylmethoxy)-2-oxabicyclo[2.2.1]heptan-4-yl)carbonylaminocarbonyl; or R and $R^1$ when taken together are =C=O; X is —C(CH$_3$)$_2$— and Y is a single bond; and $R^2$ is a phenyl group optionally substituted by one or two halogen atoms of atomic number 9 to 17 or by a methyl group, and stereoisomer forms or mixtures thereof.

2. A compound according to claim 1 wherein R is a hydrogen atom; and $R^1$ is

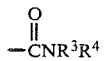

in which $R^3$ is an alkyl group contining 1 to 4 carbon atoms or an alkenyl or alkynyl group containing 3 to 4 carbon atoms and $R^4$ is a hydrogen atom; —O$R^3$ in which $R^3$ is an alkyl group containing 1 to 4 carbon atoms; —C(O)$R^3$ in which $R^3$ is an alkyl group containing 1 to 4 carbon atoms; and when $R^1$ is —C(O)$R^3$ then R is also additionally —C(O)$R^3$.

3. A compound according to claim 2 wherein $R^2$ is phenyl, 2-chlorophenyl, 2-fluorophenyl, 2-methylphenyl, 2,6-dichlorophenyl or 4-fluorophenyl.

4. A compound according to claim 3 wherein R is a hydrogen atom; and $R^1$ is

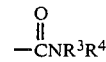

in which $R^3$ is an alkyl group of 1 to 4 carbon atoms, allyl or propargyl and $R^4$ is a hydrogen atom; —O$R^3$ in which $R^3$ is a methyl or ethyl group; or —C(O)$R^3$ in which $R^3$ is a methyl or ethyl group and when $R^1$ is —C(O)$R^3$ then R is also additionally —C(O)$R^3$.

5. A compound according to claim 4 wherein $R^2$ is phenyl, 2-fluorophenyl or 2-methylphenyl.

6. A compound according to claim 5 wherein R is H and $R^1$ is propargylaminocarbonyl.

7. A compound according to claim 5 wherein R is a hydrogen atom or an acetyl group and $R^1$ is an acetyl group.

8. A compound according to claim 1 wherein R is a hydrogen atom and $R^1$ is —P(O)(O$R^3$)$_2$ in which $R^3$ is an alkyl group containing 1 to 4 carbon atoms.

9. A compound according to claim 8 wherein $R^3$ is an ethyl group.

10. A herbicidal or plant growth regulating composition comprising an effective amount of an active compound according to claim 1 and at least one carrier or surface-active agent.

11. A method for controlling undesirable plant growth at a locus comprises applying to the locus or the plant an effective amount of an active compound according to claim 1.

12. A method according to claim 11 wherein the control is herbicidal.

* * * * *